United States Patent [19]

Kletschka et al.

[11] 4,096,864
[45] * Jun. 27, 1978

[54] FLUID CARRYING SURGICAL INSTRUMENT OF THE FORCEPS TYPE

[75] Inventors: Harold D. Kletschka, Minneapolis; Edson D. Rafferty, Excelsior, both of Minn.

[73] Assignee: Bio-Medicus, Inc., Minnetonka, Minn.

[*] Notice: The portion of the term of this patent subsequent to Nov. 4, 1992, has been disclaimed.

[21] Appl. No.: 674,916

[22] Filed: Apr. 8, 1976

Related U.S. Application Data

[63] Continuation of Ser. No. 562,126, Mar. 26, 1975, abandoned, which is a continuation of Ser. No. 446,408, Feb. 28, 1974, abandoned, which is a continuation-in-part of Ser. No. 384,461, Aug. 1, 1973, abandoned, which is a continuation of Ser. No. 198,900, Nov. 15, 1971, abandoned.

[51] Int. Cl.² .................. A61B 17/28; A61M 1/00
[52] U.S. Cl. ......................................... 128/354
[58] Field of Search ............... 128/2 F, 2 R, 2 B, 276, 128/214.4, 240, 277, 297, 346, 321, 354; 32/69

[56] References Cited

U.S. PATENT DOCUMENTS

| 2,601,513 | 6/1952 | Gladstone | 128/2 F |
|---|---|---|---|
| 3,071,402 | 1/1963 | Lasto et al. | 294/64 |
| 3,361,133 | 1/1968 | Kimberley et al. | 128/346 |
| 3,367,336 | 2/1968 | Eizenberg | 128/321 |
| 3,495,593 | 2/1970 | Snyder | 128/309 |
| 3,511,240 | 5/1970 | Williams et al. | 128/276 |
| 3,517,669 | 6/1970 | Buono et al. | 128/276 |
| 3,561,448 | 2/1971 | Peternel | 128/334 |
| 3,606,681 | 9/1971 | Rogers et al. | 128/318 X |
| 3,749,090 | 6/1973 | Stewart | 128/240 |
| 3,807,406 | 4/1974 | Rafferty et al. | 128/318 |
| 3,916,909 | 11/1975 | Kletschka et al. | 128/354 |

Primary Examiner—Robert W. Michell
Assistant Examiner—Jerome D. Stremcha
Attorney, Agent, or Firm—Merchant, Gould, Smith, Edell, Welter & Schmidt

[57] ABSTRACT

Surgical forceps are disclosed which consist of first and second legs attached at one end in a tweezer-like configuration. One of the legs includes a small conduit which terminates in one or more inlets disposed on the inner and outer surface of the tweezers. The opposite end of the conduit is adapted for connection to a source of vacuum to permit fluid to be drawn away from a surgical area. In an alternative embodiment, a similar conduit is formed in the other forceps leg which is adapted for connection to liquid under pressure, terminating in one or more openings on the inner and outer surface of the tweezer legs to permit cleansing of the surgical area. In either embodiment, the conduits are selectively extendable beyond the tip of the forcep leg by movable tubes which allow the suction of fluid supply to reach into areas removed from the forcep leg. Fluid control means are provided on the tweezers for both the vacuum conduit and the liquid supply conduit.

44 Claims, 23 Drawing Figures

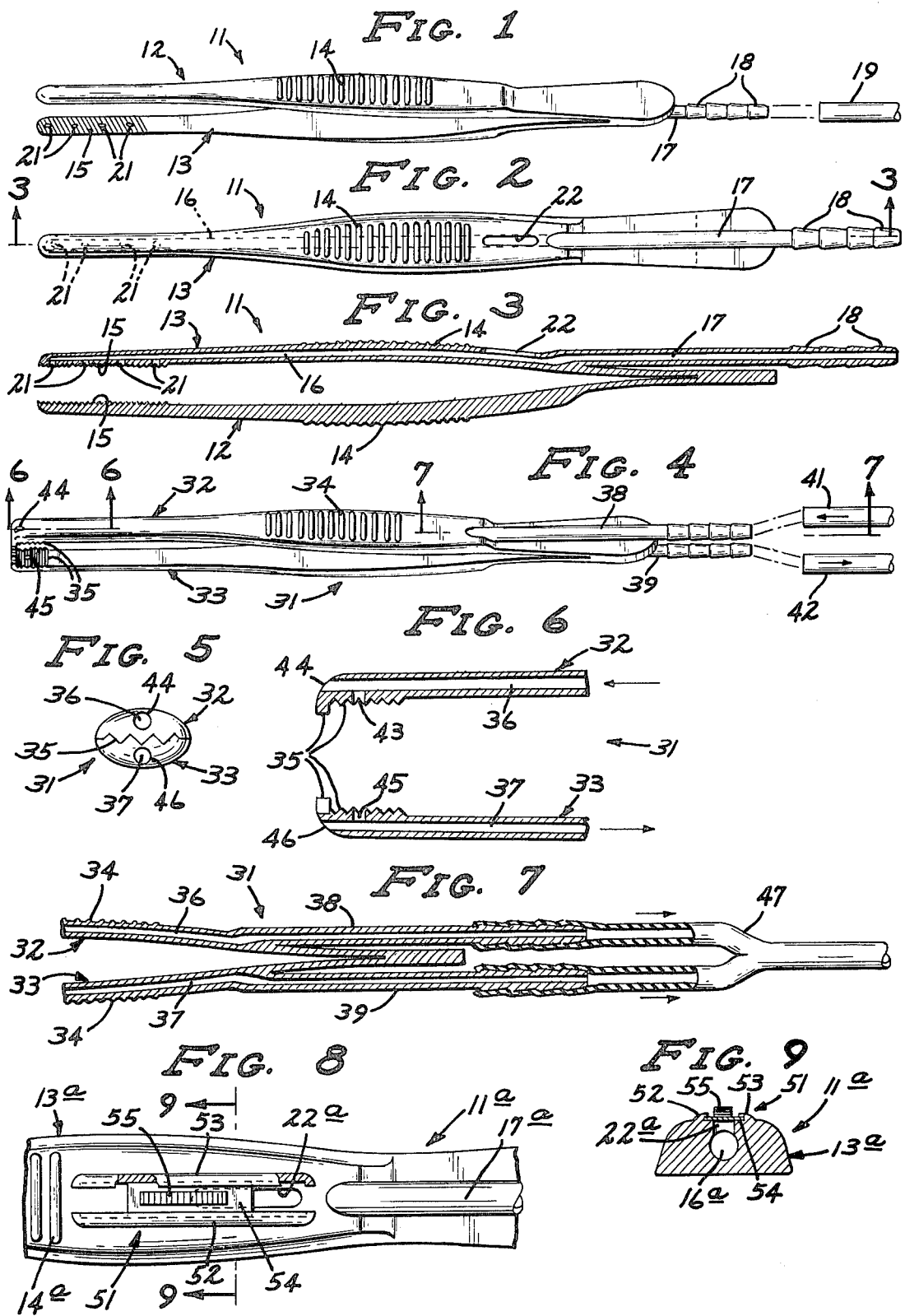

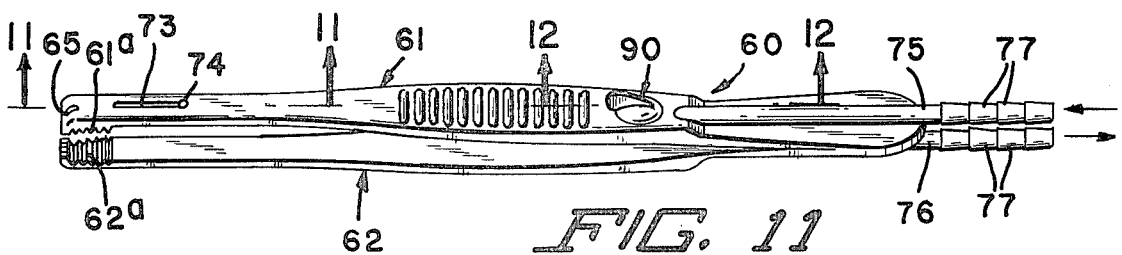
FIG. 10
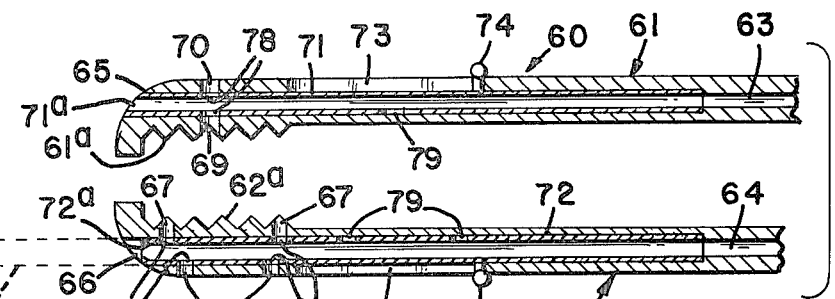
FIG. 11
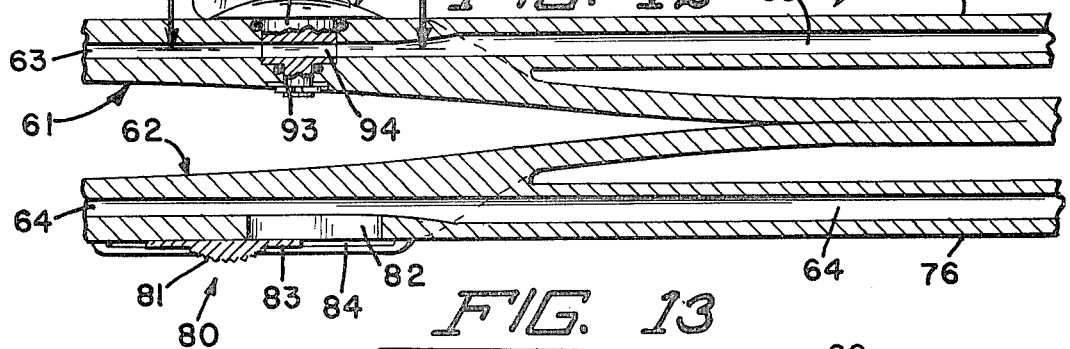
FIG. 12
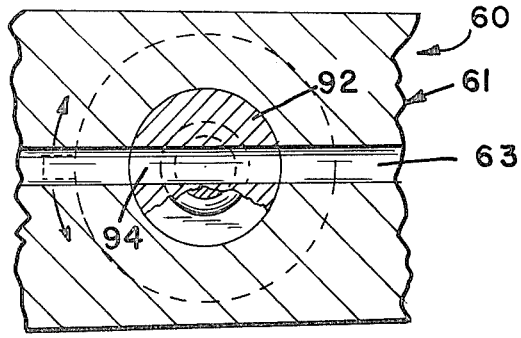
FIG. 13
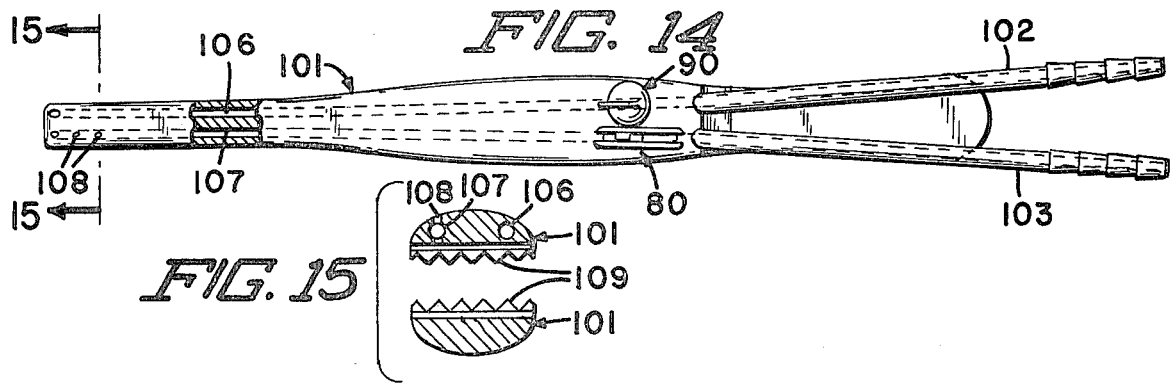
FIG. 14
FIG. 15

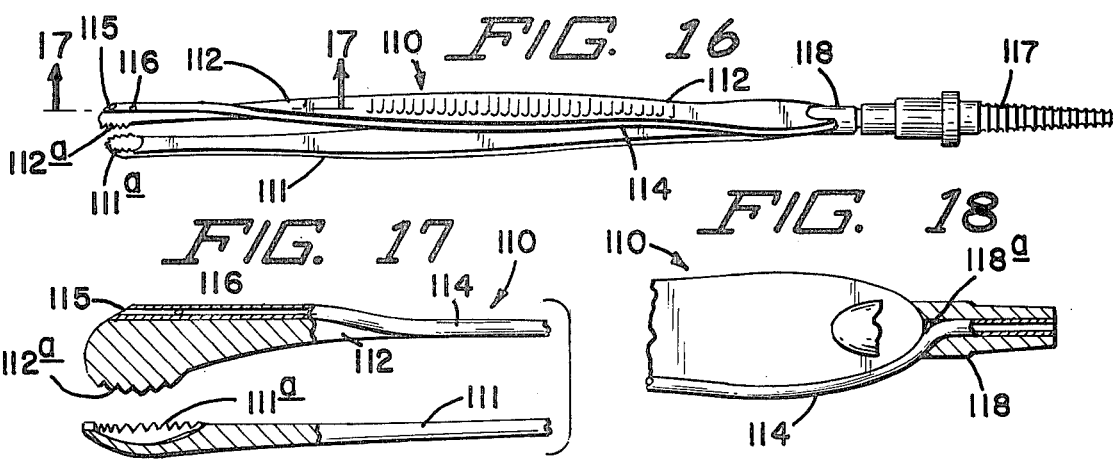
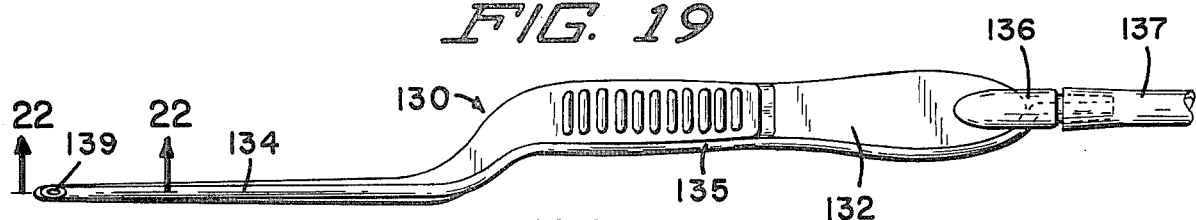
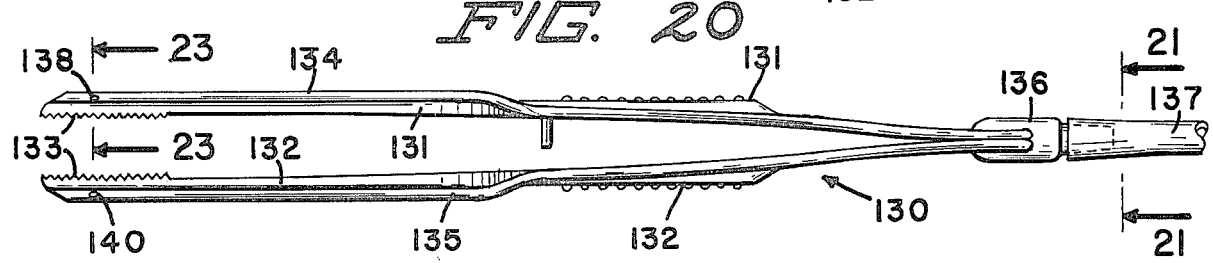
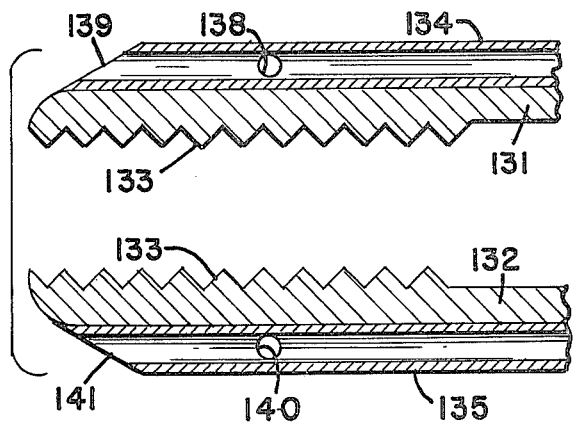
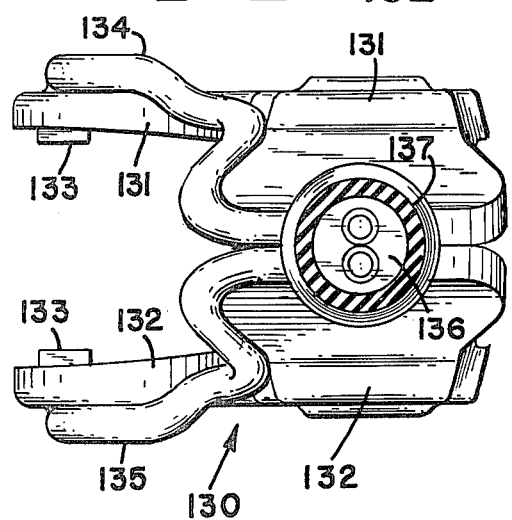
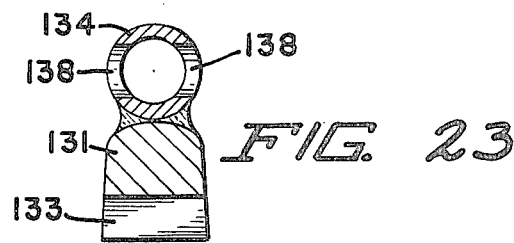

# FLUID CARRYING SURGICAL INSTRUMENT OF THE FORCEPS TYPE

This is a continuation of application Ser. No. 562,126, filed Mar. 26, 1975 and now abandoned, which was a continuation of application Ser. No. 446,408, filed Feb. 28, 1974 and now abandoned, which was a continuation-in-part of application Ser. No. 384,461, filed Aug. 1, 1973 and now abandoned, which was a continuation of Ser. No. 198,900, filed Nov. 15, 1971 and now abandoned.

SUMMARY OF THE INVENTION

The invention relates generally to surgical instruments and is specifically directed to surgical forceps of the tweezerlike configuration which includes suction means for removing the fluid and/or gases from a surgical area and fluid delivery means for cleansing a surgical area.

In surgery, a problem is often posed by the presence of blood, gases or other material in the area of the surgical incision. Such materials must be removed where they may be harmful to the surrounding tissue or where they impair the surgeon's view of the surgical area. Such material may be removed by suction means or, in some instances, must first be washed from the surrounding tissue. The presence of such fluids may be the direct result of incision, the cleansing operation described above, or an accumulation prior to entry into the area. Gases are a problem, for example, when a bovey current is being used. Where the problem arises, these fluids or gases ordinarily must be removed as quickly as possible to permit the surgeon to carry out his task with the least possible obstruction.

One solution to these problems has been the provision of a probe or similar device which is connected to a vacuum source or fluid supply and which is capable of aspirating body fluids from the surgical area or flushing the area with the liquid. However, when the surgeon is using other surgical instruments in his operative task, the suction or fluid delivery devices must be manipulated by surgical's assistant, which is often impossible or at least hindering or disrupting due to space limitation, or the surgeon must change the instruments when an accumulation of fluid or the visibility of the surgical area becomes a problem.

This invention enables the surgeon to perform the normal surgical task and the cleansing or vacuuming of accumulated fluids from the surgical area simultaneously with the single surgical instrument. The instrument comprises a surgical forceps of tweezer-like configuration. In one configuration, one leg of the instrument contains aspirating or spraying openings which communicate with a fluid conduit carried by and movable from one of the forceps legs. The conduit connects with either a source of cleansing liquid under positive pressure or a source of vacuum. In a second configuration, the opposite leg also has openings which communicate with the second conduit carried by and removable from that leg and which also connects with a source of cleansing fluid or a vacuum. The supply of a liquid or the supply of a vacuum source to either leg of the forceps may be accomplished in various combinations depending on the particular surgical need.

To prevent the complete blockage of the various openings by the tissue being held by the forceps, the openings in the forceps legs have been selectively located on both the inner and outer leg surfaces. In addition, movable tubes can be extended out from the tips of the tweezer legs to allow cleansing or suction in areas removed from the tweezers. These tubes communicate with the fluid conduit located on the tweezer legs. Valves are provided on the tweezers for regulating either the flow of cleansing liquid or the amount of vacuum applied through the various openings.

BRIEF DESCRIPTION OF THE DRAWINGS

FIG. 1 is a perspective view of surgical forceps embodying the inventive principle;

FIG. 2 is a side elevation of the surgical forceps showing the side opposite that seen in FIG. 1;

FIG. 3 is a sectional view taken along the line 3—3 of FIG. 2;

FIG. 4 is a perspective view of an alternative surgical forceps;

FIG. 5 is an end view of the surgical forceps of FIG. 4;

FIG. 6 is a fragmentary sectional view of the alternative surgical forceps taken along the line 6—6 of FIG. 4;

FIG. 7 is a fragmentary sectional view of the alternative surgical forceps taken along the line 7—7 of FIG. 4;

FIG. 8 is an enlarged fragmentary view in side elevation of an alternative structure for variably controlling the amount of applied vacuums, portions thereof being broken away and shown in section;

FIG. 9 is a sectional view taken along the line 9—9 of FIG. 8;

FIG. 10 is a perspective biew of an alternative surgical forceps;

FIG. 11 is a fragmentary sectional view of the alternative surgical forceps taken along the line 11—11 in FIG. 10;

FIG. 12 is a fragmentary sectional view of the alternative surgical forceps taken along the line 12—12 in FIG. 10;

FIG. 13 is a fragmentary sectional view of the alternative surgical forceps taken along the line 13—13 of FIG. 12 showing the fluid control valve;

FIG. 14 is a side elevation of an alternative surgical forceps;

FIG. 15 is a sectional view of the alternative surgical forceps taken along the line 15—15 in FIG. 14;

FIG. 16 is a perspective view of a Russian-style forceps;

FIG. 17 is a fragmentary section view of the Russian-style forceps, taken along the line 17—17 in FIG. 16;

FIG. 18 is an enlarged fragmentary view of the Russian-style forceps of FIG. 16;

FIG. 19 is a view in side elevation of yet another alternative surgical forceps;

FIG. 20 is a top elevational view of the surgical forceps of FIG. 19;

FIG. 21 is an enlarged end view of the alternative surgical forceps taken along the line 21—21 of FIG. 20, a portion shown in section;

FIG. 22 is an enlarged fragmentary section taken on the line 22—22 of FIG. 19; and FIG. 23 is a fragmentary sectional view of the alternative surgical forceps taken along the line 23—23 of FIG. 20.

DESCRIPTION OF THE PREFERRED EMBODIMENTS

With initial reference to FIGS. 1-3, one embodiment of a surgical forceps embodying the inventive principle is represented generally by the numeral 11. Forceps 11 has a tweezer-like configuration, consisting of a pair of elongated leg members 12, 13 which are commonly affixed at one end and project in cantilever fashion from the affixed point. Members 12, 13 are preferably formed from stainless steel for sterile purposes, and have a spring characteristic which causes the leg members to be normally biased away from each other.

The outer face of each leg member 12, 13 has an irregular surface portion 14 at an intermediate point thereon to provide a gripping surface for the user. The leg members each terminate in a functional end, such ends together cooperating to perform the forceps function. In the embodiment of FIGS. 1–3, the functional ends of leg members 12, 13 are rounded and each has a serrated portion 15 on its inner face, the teeth of such serrated portions alternately merging with the other to provide an efficient clamping or pincer function.

In FIG. 3, leg member 13 has formed therein an extended passageway or conduit 16, one end of which communicates with a tubular connector 17 rigidly affixed to leg member 13. Connector 17 terminates in a series of tapered, annular segments 18 which adapt the conduit 16 for connection to a vacuum or cleansing liquid source (not shown) through a flexible tube 19.

The opposite end of conduit 16 terminates in a plurality of bores 21 which open on the inner face of leg member 13 within the serrated portion 15. The connection of tubular connector 17 will effect an aspirating or spraying action at the bores 21, which permits the cleansing or removal of fluids and gases from a surgical area by simple exposure of the inner face of leg member 18 to the area. Where a vacuum source is connected to forceps 11, the amount of vacuum is controlled by the user by means of an opening 22 which communicates with conduit 16 and is disposed on the outer face of leg member 13 immediately rearward of irregular surface 14. If vacuum is not desired at the functional end of forceps 11, the elongated opening 22 is left uncovered. When all or part of the vacuum is deemed necessary, the user simply covers all or part of elongated opening 22.

In FIGS. 4–7, an alternative forceps embodying the inventive principle is represented generally by the numeral 31. Forceps 31 is similar to forceps 11, comprising commonly affixed leg members 32, 33 each having an irregular gripping surface 34 disposed on the outer surface thereof. The functional ends of leg members 32, 33 are somewhat more squared than those of forceps 11, in FIG. 4, and the serrated portion 35 of each extends to the extreme tip and the inner face of each functional end (see FIG. 5).

One principle modification of forceps 31 is the inclusion of conduits 36, 37 respectively, in each of the leg members 32, 33. Similarly, each of the conduits 36, 37 communicates with a tubular connector, designated 38, 39, respectively; and, by the series of tapered segments, each connector is adapted to receive a flexible tube 41, 42. As is indicated by the arrows in FIG. 4, flexible conduit 41 is connected to a source of fluid, either liquid or gas, under positive pressure for rinsing or otherwise cleansing the surgical area; and flexible tube 42 is connected to a vacuum source as described above.

In FIGS. 5 and 6, conduit 36 opens at the functional end of leg member 32 by a bore 43 disposed on the inner face within the serrated portion 35 and a bore 44 disposed at the tip of the forceps. Similar bores 45, 46 are provided for leg member 33. The location of the bores 43, 46, enable the user to apply or draw fluid, either at the inner functional face or the extreme tip of forceps 31.

In FIG. 7, the respective tubular connectors 38, 39 of forceps 31 are commonly connected to a single vacuum source by a flexible tube 47 having a bifurcated end.

FIGs. 8 and 9 disclose a modification to the vacuum control of forceps 11. The modified forceps is represented generally by the numeral 11a, and the parts corresponding to forceps 11 are designated by the same numeral with the addition of the letter a. Forceps 11a includes an elongated opening 22a to control the vacuum at its functional end, and a sliding valve assembly represented generally by the numeral 51 assists in providing a more precise control of the vacuum. Sliding valve 51 consists of a pair of elongated guiding members 52, 53 affixed to the other face of leg member 13a, each defining an elongated slot in which a sliding valve member 54 is disposed. Preferably, the fit of valve member 54 within the slots is sufficiently tight so that movement is frictional, thus permitting it to be retained in a preselected position. movement, of the sliding valve member 54 is facilitated by an irregular surface portion 55, which provides a gripping surface for the user's fingers. Sliding valve member 54, in its extended position, is fully capable of sealing elongated opening 22a; and its movement to a selected position to open, partially seal or fully seal elongated opening 22a effects control of the vacuum at the forceps tip.

In FIGS. 10–13 another alternative forceps embodiment of the inventive principle is represented generally by the numeral 60. Forceps 60 is similar to forceps 31, comprising commonly affixed leg members 61 and 62, each having a serrated portion 61a and 62a respectively on the interiors of its functional end (see FIG. 11). Conduits 63 and 64 extend through the leg members 61 and 62 and join connectors 75 and 76 respectively. Annular segments 77 adapt connectors 75 and 76 for connection to flexible tubes (not shown) leading to vacuum sources or a liquid supply under pressure.

One principal modification of forceps 60 is the arrangement of a plurality of bores and openings 65–70 located on the outer and inner surfaces of leg members 61 and 62 and on the leg member tips. Bores 69 and 70 are located on the inner and outer surfaces respectively of leg member 61. Bores 67 and 68 are located on the inner and outer surfaces respectively of tweezer-leg 62. Openings 65 and 66 are located in the rounded ends of leg members 61 and 62 respectively. This multiplicity of bore locations allows fluid to flow into or out of some of the bores even when others of the bores are blocked by tissue held between the tweezer legs or by tissue lying against the exterior of the tweezers. Thus, if bores 69 and 70 are blocked by tissue held between the tweezer legs 61 and 62, the exterior bores 67 and 68 can still perform their cleaning or vacuum functions. In a similar manner, if tissue lies against openings 68 on the exterior of leg member 61, and one of the bores 70 is blocked by tissue held between the tweezers, the other interior bore 70 can perform the desired cleaning or vacuum function.

Another principal modification of forceps 60 is the use of extension tubes 71 and 72 located in conduits 63 and 64 respectively. The purpose of extension tubes 71 and 72 is to allow the cleansing or vacuuming of areas which are removed from the ends of forceps legs 61 and 62. To accomplish this function, tubes 71 and 72 are slidably movable within conduit 63 and 64 to a position wherein openings 65 and 66 respectively are located beyond the tips of leg members 61 and 62. To slide tube extensions 71 and 72 to a position wherein a portion of them is outside of the leg members 63 and 64 respectively (shown by dotted lines in FIG. 11), a protuberance 74 is provided on both tubes 71 and 72 and extends through an opening 73 in both leg members 61 and 62. To extend the tubes 71 or 72, the protuberances 74 are urged forward in slots 73 by means of pressure from a thumb or finger. Because there is a friction fit between tube extensions 71 and 72 in conduit 63 and 64, tube extensions 71 and 72 will tend to remain in their placed position. This friction fitting may also be accomplished by providing for friction contact between protuberance 74 and the walls of slots 73.

A plurality of bores 78 are provided in extension tubes 71 and 72 to accomplish the cleansing or vacuum functions similarly performed by bores 65-70. Thus, when either or both of extension tubes 71 or 72 are in the extended position, fluid may be supplied to or extracted from a position removed from the leg members 61 and 62, independent of the other openings 65-70. This allows the cleansing or vacuuming of areas which are slightly removed from the tissue being manipulated by forceps 60. In addition, when all of the bores 65-70 are blocked by adjoining tissue, the bores 78 in extension tubes 71 and 72 may still be utilized to perform the desired function. in the embodiment shown on FIG. 11, an opening 72a is shown in the end of extension tube 72. To allow the cleansing or vacuuming of areas adjacent to the serrations 61a-62a when extension tubes 71 and 72 are extended, additional openings 79 are provided in extension tubes 71 and 72. Openings 79 are positioned on extension tubes 71 and 72 so that they index with bores 67 and 69 when extension tube 72 is in its extended position. In this position liquid can be supplied to or taken in through either of the openings 72a and 78 or through the like openings 68 and 70. Similar positioning of openings 79 may be provided in extension tube 71 (not shown in the figures). Thus, to either cleanse or remove liquid from a surgical area slightly removed from the tissue which is clamped between the legs of forceps 60, the surgeon need merely extend either or both of extension tubes 71-72, such that the openings 78 reach the desired position. In this way liquid can be taken in through either opening 78 or openings 65-70 or any combination of these openings which are not blocked by tissue. In FIG. 11, the end openings, indicated at 71a and 72a, of the extension tubes 71 and 72 respectively, are of smaller diameter than the inner diameters of the tubes 71 and 72. This arrangement prevents some pieces of more solid material from entering the tubes 71 and 72 and becoming lodged therein, or in a passage 63 or 64, and clogging these passages.

In FIGS. 12 and 13, a liquid control valve 90 or a vacuum control valve 80 may be affixed to the legs of forceps 60. The liquid control valve 90 consists of a control dial 91 affixed to a rotatable shaft 92 which extends through an opening 93 in leg member 61. A tubular opening 94 extends through to shaft 92 and may be indexed in line with passageway 63 so liquid can pass through the control valve 90. As the dial member 91 is rotated, tubular opening 94 is rotated partially out of alignment with conduit 63 and a smaller amount of liquid passes through the liquid control valve 90. When the dial 91 is set in a particular position, tubular opening 94 may be positioned completely out of line with conduit 63 and no liquid will pass through the liquid control valve 90.

To control the amount of vacuum which reaches the end of conduits 63 or 64, a vacuum control valve 80 is provided in FIG. 12. Vacuum control valve 80 is similar to the vacuum control valve 51 in FIG. 8 and consists of a thumb operated slide member 61 which moves in a rail member 84. As slide member 81 moves in rail member 84, it operates to cover an opening 82 in leg member 62 which adjoins conduit 64. Thus, as slide member 83 is moved out of the way of opening 82, the vacuum is drawn through opening 82 and little vacuum is drawn through the opening in the ends of leg members 62. When slide member 83 is positioned to cover the opening 82, a larger amount of vacuum is applied to the ends of conduits 64 and more vacuum pressure is applied at that point. While the liquid control valve 90 is shown on forceps leg member 62 and the vacuum control valve 80 is shown on forceps leg member 62, these valves may be located on either leg of forceps 60 and in any combination.

FIG. 14 shows forceps 100 which are another embodiment of the inventive principal. In this embodiment, two tubular connectors 102 and 103 are attached to one leg member 101 of forceps 100. Tubular connectors 102 and 103 join conduits 106 and 107 respectively which extend throught the leg member 101 as is shown in detail in FIG. 15. Bores 108 extend to the interior and to the exterior leg members 101 and connect with conduit 107. Other openings similar to those shown in FIGS. 10-12 may also be used where desirable. In FIG. 14, a liquid control valve 90 and a vacuum control valve 80 may be provided on forceps 100 to control the flow of fluids through conduits 106 and 107. The embodiment in FIGS. 14 and 15 is particularly useful where the vacuum function is intended primarily to remove the liquid provided by the cleaning function. In such an operation, it would be particularly useful if the means for removing liquid are placed very close to the cleaning means which add liquid to the surgical area.

FIGS. 16-18 show a Russian style forceps 110 which incorporate the inventive principle. Forceps 110 comprise like members 111 and 112 which are joined together at one end to form a tweezer-like forceps. The functional ends of leg members 111 and 112 contain serrated grasping portions 111a and 112a respectively. In FIG. 17, grasping portion 111a is a cup-like member and grasping portion 112a is a bulbous member which fits into grasping portion 111a. A single conduit 114 extends from the point where leg members 111 and 112 join to the functional end of leg member 112. An opening 115 in the end of conduit 114 and an opening 116 in the side of conduit 114 near the bulbous element 112a allow liquid to be vacuumed from the area adjacent to the forceps end or cleansing fluid applied in that area. Because of this location for openings 115 and 116, tissue which is held between the grasping portions 111a and 112a will not prevent the flow of liquids into or out of the openings. A junction element 118 is affixed to the leg members 111 and 112 where they are joined. Junction element 118 can be welded or otherwise affixed to leg members 111 and 112. The conduit 114 extends through junction element 118 into a connector 117 which is attached to the junction element 118. The conduit 114 extends through junction element 118 rather than merely join with a bore in junction element 118 to reduce the likelihood of clogging at sharp corners where the conduit 114 would meet the bore 118a.

FIGS. 19-23 show forceps 130 which also embody the inventive principle. In FIG. 20, the forceps 130 comprise two like members 131 and 132 which are joined together at one end and which have serrations 133 at their function ends. Two separate conduits 134 and 135 extend along the length of leg members 131 and 132 respectively from their point of junction to their function ends.

Conduits 134 and 135 take the form of circular tubes, terminating in end openings 139 and 141, each of which is disposed proximate the tip or extreme functional end of its associated elongated member. The opening 139 lies in and is defined by an oblique plane which transects the conduit tube 134, so that opening 139 is elliptical in shape and of greater cross sectional size than the perpendicular cross section of the conduit tube 134. As shown, the oblique plane is inclined toward the extreme end of elongated member 131, so that the end of conduit tube 134 tapers relative to elongated member 131.

Spaced from an opening 139 are a pair of transverse openings 138, which are formed through the wall of conduit tube 134. The transverse openings are of lesser cross sectional size than the end opening 139, and they are preferably disposed in transverse alignment, thus being respectively accessible from opposite sides of elongated member 131. Conduit tube 135 is constructed in the same manner, being rigidly affixed to the exterior of leg member 132, and including a like elliptical fluid opening 141 and transverse openings 140. The transverse openings 138, 140 allow the passage of fluid through the conduit tubes 134, 135 even when openings 139, 141 are blocked by surrounding tissue or other obstructions. Similarly, when openings 138, 140 are blocked, openings 139, 141 may still be opened for the passage of fluid.

FIG. 21 is an end-on-view of forceps 130 showing the route taken by conduits 134 and 135 as they extend along the forcep leg members 131 and 132 respectively. The use of an externally attached conduit 134 and 135 allow the forcep leg members 131 and 132 to be constructed with the proper amount of resilience and spring in the leg members without concern for including a conduit therein.

What is claimed is:

1. Surgical forceps of a tweezer-like configuration, comprising:
   (a) first and second elongated leg members of essentially the same length and having functional ends defining opposed inner and outer faces, said inner faces being substantially adjacent each other in the closed position, the leg members being commonly affixed and projecting from the fixed point in cantilever fashion with the functional ends normally biased apart and cooperable to perform forceps functions;
   (b) a fluid passageway at least a part of which is formed within the first elongated member, the passageway extending through the extreme functional end of the first elongated member to define a fluid opening at the tip thereof;
   (c) the passageway being adapted for connection to a source of fluid pressure;
   (d) an extensible tube having open first and second ends slideably contained within said passageway, the extensible tube being slideably movable between a retracted position, in which it is contained entirely within the passageway, and an extended position, in which the first open end of the extensible tube is disposed beyond the passageway and the second open end of the extensible tube is contained within the passageway;
   (e) and tube advance means for slideably moving the extensible tube between said extended and retracted positions to allow pressure transmitted through the passageway to be extended by the extensible tube beyond the extreme functional end of the first elongated member.

2. The surgical forceps defined by claim 1, wherein:
   (a) the first elongated member further comprises at least one fluid opening disposed on its inner face in fluid communication with said passageway;
   (b) and the extensible tube comprises at least one fluid opening formed in the side thereof and disposed for registration with the fluid opening in the inner face of the first elongated member with the extensible tube in its extended position.

3. The surgical forceps defined by claim 2, wherein the first elongated member comprises a plurality of said inner face fluid openings, and the side opening of the extensible tube is disposed for registration with at least one of said inner face fluid openings with the extensible tube in its extended position, and for registration with at least one of said inner face fluid openings with the extensible tube in its retracted position.

4. The surgical forceps defined by claim 2, wherein:
   (a) the first elongated member further comprises at least one fluid opening disposed on its outer face in fluid communication with said passageway;
   (b) and the extensible tube comprises at least one fluid opening formed in the side thereof and disposed for registration with the fluid opening in the outer face of the first elongated member with the extensible tube in its extended position.

5. The surgical forceps defined by claim 1, wherein:
   (a) the first elongated member further comprises at least one fluid opening disposed on its outer face in fluid communication with said passageway;
   (b) and the extensible tube comprises at least one fluid opening formed in the side thereof and disposed for registration with the fluid opening in the outer face of the first elongated member with the extensible tube in its extended position.

6. The surgical forceps defined by claim 1, wherein the tube advance means comprises:
   (a) an elongated slot-like opening in the functional end of the first elongated member, said slot-like opening generally adjacent a portion of said extensible tube;
   (b) and a thumb member attached to said extensible tube and extending through said slot-like opening to allow the movement of said extensible tube the length of said slot-like opening by the urging of said thumb member forward and backwards in said slot-like opening to thereby position the extensible tube in a selected position.

7. The surgical forceps defined by claim 1, and further comprising:
   (a) a second fluid passageway at least part of which is formed within the second elongated member, the passageway extending through the extreme functional end of the second elongated member to define a fluid opening at the tip thereof;
   (b) the second passageway being adapted for connection to a source of fluid pressure;
   (c) a second extensible tube having open first and second ends slideably contained within said second passageway, the second extensible tube being slideably movable between a retracted position, in which it is contained entirely within the second passageway, and an extended position, in which the first open end of the second extensible tube is disposed beyond the second passageway and the second open end of the second extensible tube is contained within the second passageway;

(d) and tube advance means for slideably moving the second extensible tube between said extended and retracted positions to allow pressure transmitted through the second passageway to be extended by the second extensible tube beyond the extreme functional end of the second elongated member.

8. The surgical forceps defined by claim 7, wherein:
(a) the second elongated member further comprises at least one fluid opening disposed on its outer face in fluid communication with said second passageway and at least one fluid opening disposed on its inner face in fluid communication with said second passageway;
(b) and the second extensible tube comprises at least one fluid opening formed in the side thereof and disposed for registration with the fluid opening in the inner face of the second elongated member with the second extensible tube in its extended position.

9. Surgical forceps of a tweezer-like configuration, comprising:
(a) first and second elongated leg members of essentially the same length and having functional ends defining opposed inner and outer faces, said inner faces being substantially adjacent each other in the closed position, the leg members being commonly affixed and projecting from the fixed point in cantilever fashion with the functional ends normally biased apart and cooperable to perform forceps functions;
(b) fluid conduit means associated with at least one of the first and second elongated members, the conduit means terminating in at least one fluid opening disposed on the inner face of the first elongated member, and at least one fluid opening disposed on the outer face of the first elongated member;
(c) the fluid conduit means being adapted for connection with a source of fluid pressure.

10. The surgical forceps defined by claim 9, wherein the fluid conduit means terminates in a plurality of fluid openings disposed on the outer face of the first elongated member, one of said fluid openings being disposed at the extreme functional end or tip of the first elongated member.

11. The surgical forceps defined by claim 10, wherein the conduit means defines a passageway part of which is formed within the first elongated member, the passageway extending through the extreme functional end of the first elongated member to define said tip opening, said other openings comprising bore-like passages extending transversely of the passageway from the inner and outer faces, respectively, and in fluid communication therewith.

12. The surgical forceps defined by claim 11, wherein at least one transverse, bore-like passage extends from the inner face through the passageway to the outer face of the first elongated member.

13. The surgical forceps defined by claim 9, and further comprising adjustable valve means for controlling the magnitude of pressure differential communicated through the first conduit means.

14. The surgical forceps defined by claim 13, wherein the adjustable valve means comprises a valve member rotatably mounted on the first elongated member and extending through the conduit means, the valve member having a fluid passage formed therein which is rotatably registrable with the conduit means to permit the passage of fluid therethrough, and rotatable to a position blocking the passage of fluid through the conduit means.

15. The surgical forceps defined by claim 9, and further comprising:
(a) second fluid conduit means associated with the other of said first and second elongated members, the second fluid conduit means terminating in at least one fluid opening disposed on the inner face of the second elongated member, and at least one fluid opening disposed on the outer face of the second elongated member;
(b) the second fluid conduit means being adapted for connection with a source of fluid pressure.

16. The surgical forceps defined by claim 15, wherein the second fluid conduit means terminates in a plurality of fluid openings disposed on the outer face of the second elongated member, one of said fluid openings being disposed at the extreme functional end or tip of the second elongated member.

17. The surgical forceps defined by claim 16, wherein the second fluid conduit means defines a passageway part of which is formed within the second elongated member, the passageway extending through the extreme functional end of the second elongated member to define said tip opening, said other openings comprising bore-like passages extending transversely of the passageway from the inner and outer faces, respectively, and in fluid communication therewith.

18. The surgical forceps defined by claim 17, and further comprisng adjustable valve means for controlling the magnitude of pressure differential communicated through the first conduit means.

19. The surgical forceps defined by claim 18, wherein the adjustable valve means comprises:
(a) a slot-like opening formed in the second elongated member and communicating with the second fluid conduit means;
(b) and a slide member movably mounted over said slit-like opening for partially covering said slot-like opening to control the magnitude of fluid pressure differential conveyed through the second fluid conduit means, the slide member being movable in response to urging by finger force.

20. Surgical forceps of a tweezer-like configuration, comprising:
(a) first and second elongated leg members of essentially the same length and having functional ends defining opposed inner and outer faces, said inner faces being substantially adjacent each other in the closed position, the leg members being commonly affixed and projecting from the fixed point in cantilever fashion with the functional ends normally biased apart and cooperable to perform forceps functions;
(c) first and second fluid conduit means respectively associated with the first and second elongated members, each of said conduit means terminating in an opening in the distal outer face of the associated elongated member at the extreme functional end thereof;

(c) said first fluid conduit means being adapted for connection to a source of negative fluid pressure;

(d) and the second fluid conduit means being adapted for connection to a source of positive fluid pressure.

21. The surgical forceps defined by claim 20, wherein each of said first and second elongated members further comprises at least one fluid opening disposed on the inner face thereof in fluid communication with the associated conduit means.

22. The surgical forceps defined by claim 20, wherein each of said first and second elongated members comprises at least one fluid opening disposed on the outer face thereof in fluid communication with the associated conduit means.

23. The surgical forceps defined by claim 22, wherein each of said first and second elongated members further comprises at least one fluid opening disposed on the inner face thereof in fluid communication with the associated conduit means.

24. The surgical forceps defined by claim 20, and further comprising first and second adjustable valve means respectively associated with said first and second fluid conduit means for controlling the magnitude of fluid pressure communicated therethrough.

25. The surgical forceps defined by claim 24, wherein the first adjustable valve means comprises:

(a) a slot-like opening formed in the second elongated member and communicating with the second fluid conduit means;

(b) and a slide member movably mounted over said slot-like opening for partially covering said slot-like opening to control the magnitude of fluid pressure differential conveyed through the second fluid conduit means, the slide member being movable in response to urging by finger force.

26. The surgical forceps defined by claim 24, wherein the second adjustable valve means comprises adjustable valve means for controlling the magnitude of pressure differential communicated through the first conduit means.

27. Surgical forceps of a tweezer-like configuration, comprising:

(a) first and second elongated leg members of essentially the same length and having functional ends defining opposed inner and outer faces, said inner faces being substantially adjacent each other in the closed position, the leg members being commonly affixed and projecting from the fixed point in cantilever fashion with the functional ends normally biased apart and cooperable to perform forceps functions;

(b) first conduit means associated with the first elongated member and terminating in at least one fluid opening disposed in the outer face at the distal end thereof;

(c) second fluid conduit means associated with the first elongated member and terminating in at least one fluid opening disposed in the outer face at the distal end thereof;

(d) the first and second fluid conduit means being adapted for connection with a source of fluid pressure.

28. The surgical forceps defined by claim 27, wherein the second fluid conduit means comprises a plurality of fluid openings disposed on the outer face of said first elongated member.

29. The surgical forcep defined by claim 27, wherein the first and second fluid conduit means are respectively connected to sources of positive and negative fluid pressure.

30. The surgical forceps defined by claim 29, and further comprising first and second adjustable valve means respectively associated with the first and second fluid conduit means for controlling the magnitude of fluid pressure communicated therethrough.

31. The surgical forceps defined by claim 30, wherein the first adjustable valve means comprises a valve member rotatably mounted on the first elongated member and extending through the conduit means, the valve member having a fluid passage formed therein which is rotatably registrable with the conduit means to permit the passage of fluid therethrough, and rotatable to a position blocking the passage of fluid through the conduit means.

32. The surgical forceps defined by claim 30, wherein the second adjustable valve means comprises:

(a) a slot-like opening formed in the second elongated member and communicating with the second fluid conduit means;

(b) and a slide member movably mounted over said slot-like opening for partially covering said slot-like opening to control the magnitude of fluid pressure differential conveyed through the second fluid conduit means, the slide member being movable in response to urging by finger force.

33. A suction surgical instrument comprising:

(a) at least one elongated leg member of predetermined length and having a functional end constructed to perform a surgical function;

(b) a fluid conduit tube externally affixed to at least a portion of said elongated leg member, said fluid conduit tube being adapted for connection to a source of fluid pressure;

(c) said fluid conduit tube terminating in an open end of predetermined cross sectional size disposed proximate the extreme functional end of said one elongated member, said open end lying in a substantially oblique plane which transects the fluid conduit tube, whereby the cross sectional size of the open end is greater than the internal perpendicular cross sectional size of the fluid conduit tube;

(d) and first and second transverse openings formed through the wall of the fluid conduit tube in a position spaced from said open end, said transverse openings being of lesser cross sectional size than said open end and disposed on opposite sides of the fluid conduit tube.

34. The surgical instrument defined by claim 33, wherein the fluid conduit tube is circular in cross section, and the open end is elliptical in shape.

35. The surgical instrument defined by claim 33, wherein the oblique plane in inclined toward the extreme end of said one elongated member so that the end of the fluid conduit tube tapers relative to said one elongated member.

36. The surgical instrument defined by claim 33, wherein said transverse openings are disposed in transverse alignment and are respectively accessible from opposite sides of said one elongated member.

37. A suction surgical instrument comprising:

(a) first and second elongated leg members of essentially the same length and having functional ends defining opposed inner and outer faces, said inner faces being substantially adjacent each other in the closed position, the leg members being commonly affixed and projecting from a fixed point in cantilever fashion with the functional ends normally biased apart and cooperable to perform forceps functions;

(b) a fluid conduit tube affixed to at least a portion of one of said elongated leg members, and adapted for connection to a source of fluid pressure;

(c) said fluid conduit tube terminating in an open end of predetermined cross sectional size disposed proximate the extreme functional end of said one elongated member;

(d) and at least one transverse opening formed through the wall of the fluid conduit tube at a point spaced from said open end, said transverse opening being of lesser cross sectional size than said open end.

38. The surgical instrument defined by claim 37, wherein the fluid conduit tube is externally affixed to the first elongated member over substantially the entirety of its length, and further comprising a fluid connector member integrally affixed to the forceps and communicating with the fluid conduit tube, the connector member being adapted for connection with the source of fluid pressure.

39. The surgical instrument defined by claim 37, and further comprising:

(a) a second fluid conduit tube externally affixed to at least a portion of the other of said first and second elongated members, said second conduit tube being adapted for connection to a source of fluid pressure;

(b) the second fluid conduit tube terminating in an open end of predetermined cross sectional size disposed proximate the extreme functional end of the second elongated member;

(c) and at least one transverse opening formed through the wall of the second fluid conduit tube at a point spaced from said open end, said transverse opening being of lesser cross sectional size than said open end.

40. The surgical instrument defined by claim 37, wherein the open end of the fluid conduit tube lies essentially in an oblique plane which transects the fluid conduit tube, whereby the oblique cross sectional size of the open end is greater than the internal perpendicular cross sectional size of the fluid conduit tube.

41. The surgical instrument defined by claim 40, wherein the fluid conduit tube is circular in cross section, and the open end is elliptical in shape.

42. The surgical instrument defined by claim 40, wherein the oblique plane is inclined toward the extreme end of said one elongated member so that the end of the fluid conduit tube tapers relative to said one elongated member.

43. The surgical instrument defined by claim 37, in which two such transverse openings are formed through the wall of the fluid conduit tube and disposed on opposite sides thereof.

44. The surgical instrument defined by claim 43, wherein said transverse openings are disposed in transverse alignment and respectively accessible from opposite sides of said one elongated member.

* * * * *